(12) United States Patent
Jariwalla

(10) Patent No.: US 6,468,980 B1
(45) Date of Patent: Oct. 22, 2002

(54) METHODS AND COMPOSITIONS FOR POTENTIATING CANCER CHEMOTHERAPEUTIC AGENTS

(75) Inventor: Raxit J. Jariwalla, Saratoga, CA (US)

(73) Assignee: Oxycal Laboratories, Inc., Prescott, AZ (US)

( * ) Notice: Subject to any disclaimer, the term of this patent is extended or adjusted under 35 U.S.C. 154(b) by 0 days.

(21) Appl. No.: 09/654,377

(22) Filed: Sep. 1, 2000

(51) Int. Cl.$^7$ .................................................. A61K 31/70
(52) U.S. Cl. .......................................... 514/34; 514/474

(58) Field of Search .................................... 574/34, 474

(56) References Cited

FOREIGN PATENT DOCUMENTS

| WO | WO8703481 | * | 6/1987 |

* cited by examiner

Primary Examiner—Elli Peselev
(74) Attorney, Agent, or Firm—Drummond & Duckworth

(57) ABSTRACT

The effect of cancer chemotherapeutic agents is potentiated by combination with mineral ascorbates, Vitamin C metabolites and/or Vitamin C-derived furanones.

6 Claims, 3 Drawing Sheets

METHODS AND COMPOSITIONS FOR POTENTIATING CANCER CHEMOTHERAPEUTIC AGENTS

This invention relates to methods and compositions for potentiating the effectiveness of cancer chemotherapeutic agents.

In another respect, the invention pertains to such methods and compositions which permit one to increase the effectiveness of cancer chemotherapeutic agents, such that these agents can be used at lower dose rates, without sacrificing the efficacy of the agent.

In still another aspect, the invention concerns cancer chemotherapeutic compositions which include a combination of chemotherapeutic components which either cause cancer cell apoptosis or reduced proliferation rate or both.

Numerous cancer chemotherapeutic agents are known. In many cases, however, the administration of such agents at effective dose rates cause undesirable side effects which severely limit their utility. Accordingly, it would be highly desirable to provide methods and compositions that would potentiate the chemotherapeutic effects of such agents, such that they could be effectively administered at lower dose rates, thereby reducing or eliminating such undesired side effects.

I have now discovered that the effect of cancer chemotherapeutic agents is significantly potentiated by formulating them with a potentiating component which is a member selected from the group consisting of a mineral ascorbates, Vitamin C metabolites and Vitamin C-derived furanones. By this technique, the same cancer chemotherapeutic effect is attained at significantly lower dose rates, in some cases at dose rates only about one-tenth of that required if the chemotherapeutic agent alone is administered.

Figure 1:
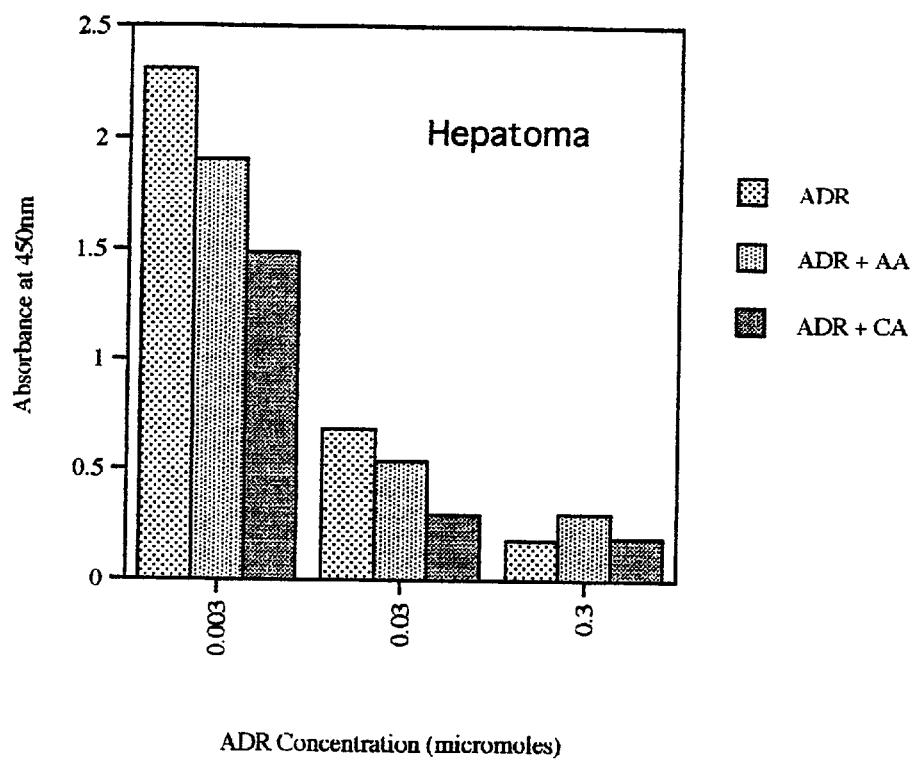
FIG. 1 is a histogram showing that the combined treatment of doxorubicin (a.k.a. Adriamycin (ADR)) with adjuvant Ascorbic Acid (AA) or Calcium Ascorbate (CA) gave greater suppression of hepatoma proliferation than doxorubicin alone.

In the presently preferred embodiment of the invention I provide a composition comprising doxorubicin (adriamycin) and a member selected from the group consisting of plasma soluble mineral ascorbates, Vitamin C metabolites and Vitamin C-derived furanones. The mineral ascorbate is a non-toxic metal ascorbate, e.g., calcium ascorbate, sodium ascorbate, zinc ascorbate, magnesium ascorbate and the like. The Vitamin C metabolites include dehydroascorbic acid, threose, erythreose, 3-hydroxy kojic acid, 5-hydroxymaltol, aldonic acids, e.g., threonic, xylonic and lyxonic acids and non-toxic mineral salts thereof, e.g., calcium threonate, and corresponding aldono-lactones and lactides. The Vitamin C-derived furanones include, illustratively, 4-hydroxy-5methyl-3(2H)-furanone and related furanones.

The methods of the present invention comprise administering a cancer chemotherapeutic dose, as a single dose or in repeated doses, of the above-described potentiated cancer chemotherapeutic compositions. Administration can be by any suitable technique normally used to administer cancer chemotherapeutic agents, e.g., orally or by parenteral injection.

EXAMPLE

The following procedures are carried out to demonstrate the activity of calcium ascorbate (CA), calcium ascorbate-calcium threonate compositions (CA+CT), calcium ascorbate-metabolites-furanone compositions (CA+CT+FR) and a commercially available calcium ascorbate-metabolites-furanone composition (EC) available under the trademark Ester-C® from Inter-Cal Corporation, Prescott, Ariz., USA.

Methods

Ascorbate/Metabolites

Calcium ascorbate (CA), calcium threonate (CT), 4-hydroxy-5-methyl-3(2H)-furanone (FR) and Ester-C (EC) are obtained from Inter-Cal Corporation, Prescott, Ariz., USA. Tissue culture grade Ascorbic acid (AA) is from Sigma Chemical Company, St. Louis, Mo., USA. The composition of calcium ascorbate (calcium di-(L-ascorbate) dihydrate) is made by sequentially dissolving individual components in sterile water to obtain master-stock solutions of equal strength (1% w/v). Aqueous solution of calcium ascorbate plus calcium threonate plus 4-hydroxy-5-methyl-3(2H)-furanone (CA/CT/FR) is prepared at ratio of 85/7.5/7.5. For comparative analysis, stock solutions containing identical ascorbic acid (AA) equivalents are used. All master stocks are stored at room temperature during the course of these procedures. From these, 10× strength working stocks are prepared by serial dilution on the day of use and are applied to cells in microtiter plates as described below.

Chemotherapeutic Agent

Adriamycin (doxorubicin) is obtained from Sigma Chemical Company (St. Louis, Mo.). Stock solutions are made by dissolving adriamycin (ADR) in sterile water and DTIC in water or dilute acetic acid solution (0.01N). Stocks are stored frozen at −10 C and thawed prior to use. Serial dilutions are made in sterile water to obtain 10× strength solutions and 0/1 volume of this is applied to cells at the time of treatment.

Cells and Culture Conditions

Target human tumor-derived or normal lines consist of SK-Hep-1, a liver adenocarcinoma (hematoma) and Malme-3M, a malignant melanoma. All seed cultures are obtained from ATCC, Mannassas, Va., USA and are propagated/maintained in serum-containing growth medium in a humidified incubator of 5% $CO_2$/95% air. SH-Hep-1 cells are grown in Eagle's minimum essential medium (EMEM) in Earle's salts plus non-essential amino acids supplemented with 10% FBS plus antibiotics and Malme-3M cells are cultured in McCoy's medium supplemented with 15% fetal bovine serum (FBS) plus antibiotics.

Combinatorial Treatments and BrdU Assay Procedures

For treatment, exponentially growing cells are seeded at a density of $1\times10^4$ cells per well of 96-well microtiter plate in 0.1–0.2 ml of growth medium. After overnight cell attachment at 37 C, duplicate wells are exposed to various treatments by direct application of one-tenth volume of 10× strength solution. For treatments involving chemotherapeutic agent, one-tenth volume of serial dilutions of adriamycin (0.0006–3.0 micromolar) are applied to wells followed by application of ascorbate-containing composition (adjuvant) or sterile water (control). The adjuvant treatment is repeated every other day or on the third day (as applicable) without change of growth medium. Untreated controls receive an equivalent amount of sterile water. After 2–3 treatments with adjuvant, cells are labeled with BudR as described below. (In some experiments, wells are refed an equal volume of growth medium prior to additional of BudR. This gives a higher amount of BrdU incorporation into DNA relative to no refluiding).

For DNA labeling, the following procedure are adapted and modified from the Cell Proliferation ELISA, BudR (Colorimetric) assay of Roche Diagnostics, Indianapolis, IN, USA: Each treated well is exposed to one-tenth volume of 10× BrdU-containing medium and reincubated and 37 C overnight (15–20 hrs.). One set of control wells is exposed to medium only (no BudR) to obtain an absorbance-control (substrate only) blank for the assay. After the labeling period, the culture medium is removed and the cells are fixed and DNA denatured in one step by adding FixDenat (30 min at RT). Then, FixDenat is removed, the anti-BrdU-peroxidase reagent is added and incubation continues for 90 min at RT. After removal of the latter, the plate is washed 3 times, followed by addition of substrate solution. The plate is kept at RT until color development became sufficient for photometric detection (5–10 min). At this time, reaction is stopped by addition to each well of 25 microliter 1M sulfuric acid followed by mixing for approximately 1 min on the shaker. The absorbance of the samples is measured in an ELISA reader at 450 nm, within 5 minutes after adding stop solution. The $OD_{450nm}$ is a measure of the level of BudR incorporation into DNA, which is proportional to rate of cell proliferation. For data analysis, the mean of the absorbance is plotted against concentration of chemotherapeutic drug for each treatment to obtain a dose-response relationship of the anti-proliferative effect.

Results

Figure 2:
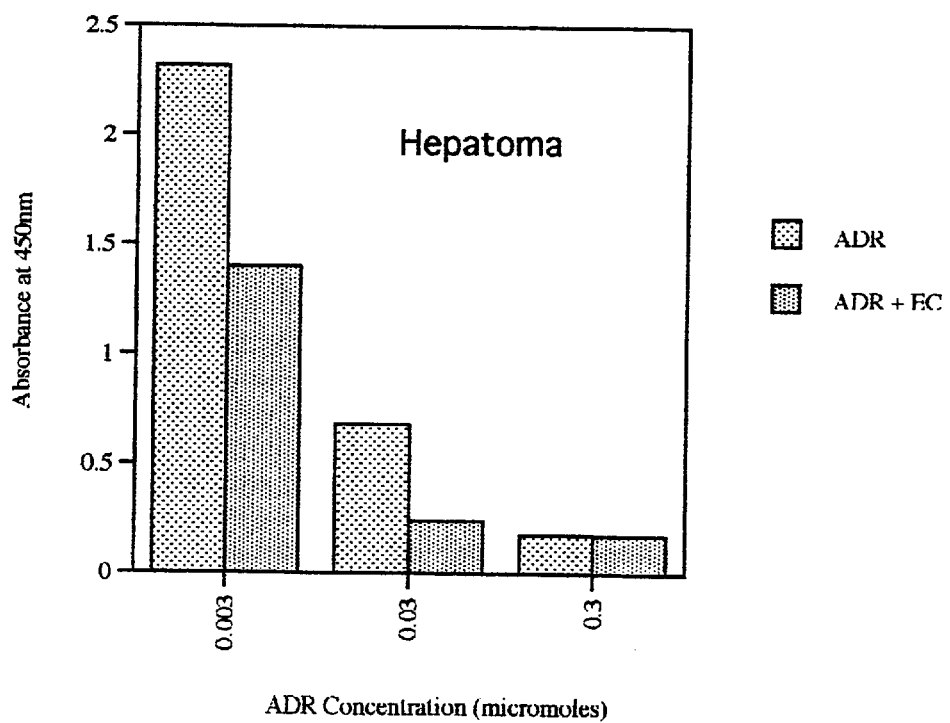
FIG. 2 is a histogram showing that a combined treatment with doxorubicin with Ester C (EC) gave greater suppression of hepatoma proliferation than doxorubicin alone.
Figure 3:
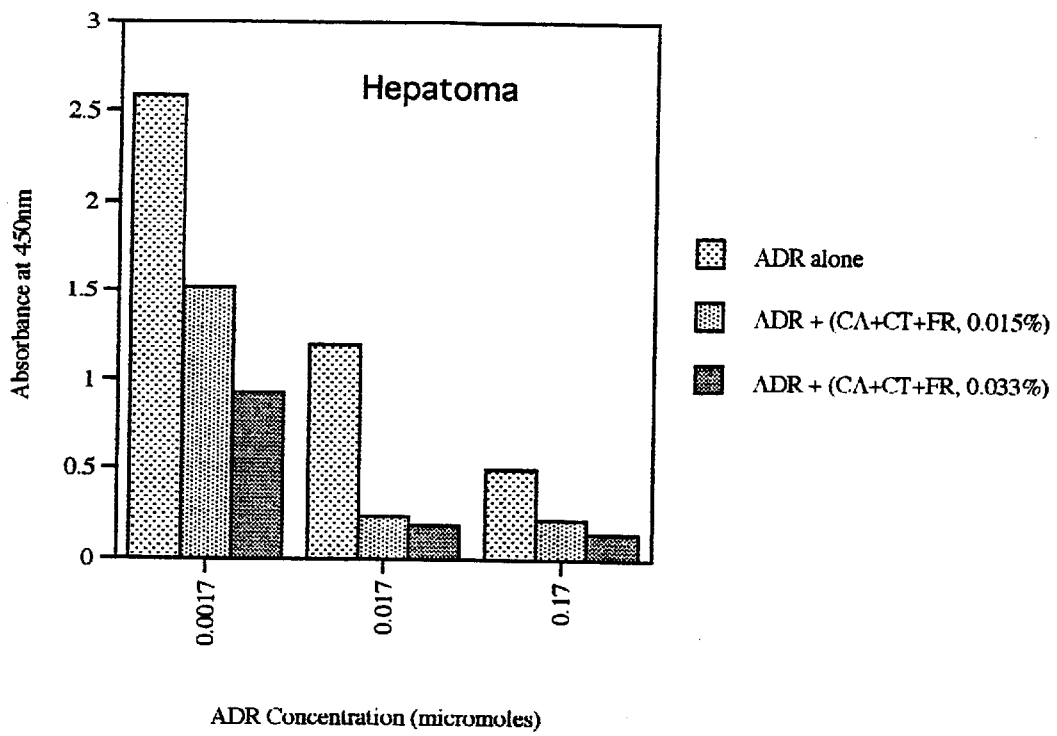
FIG. 3 is a histogram showing the combined treatments with doxorubicin with varying amounts (%) of added ascorbate metabolites mixture comprising: Calcium Ascorbate (CA), Calcium Threonate (CT), and 4-Hydroxy-5methyl-3 (2H)-furanone (FR) in the following respective ratio, 85:7.5:75.

Influence of Ascorbate, Ester-C and Triple Ascorbate plus Metabolites Combination on Anti-Neoplastic Activity of Adriamycin Against Hepatoma Cells FIG. 1 shows the effect of adriamycin (ADR) alone, ADR plus 0.5 mM ascorbic acid and ADR plus calcium ascorbate (0.5 mM AA equivalents) following one application of ADR and two applications of adjuvant (i.e. AA or CA). Note that combined treatment with adjuvant (AA or CA) gives greater suppression of hepatoma proliferation than ADR alone. The enhancing effect is prominent at low to moderate doses of ADR (0.003–0.03 micromolar) compared to higher ADR dose (0.3 micromolar). Calcium ascorbate is more effective than ascorbic acid. Similar type of hepatoma suppression is seen with ADR plus Ester-C (containing 0.5 nM AA equivalents) in the same test (FIG. 2).

In another procedure, the effects of a triple ascorbate metabolites combination (CA+CT+FR @ ratio of 85:7.5:7.5) on ADR activity is evaluated in parallel with CA or EC. FIG. 2 shows the influence of 2 different concentration s (0.015% and 0.033%) of the triple mixture following one application of ADR and three applications of the mix. As can be seen from the graph, greater proliferation of hepatoma cells occurs following ADR+triple combination compared to ADR alone. Again, the enhancing effect is more prominent at low to moderate doses (0.0017–0.017 micromolar) of ADR than the higher dose (0.17 micromolar) ADR tested.

Figure 4:
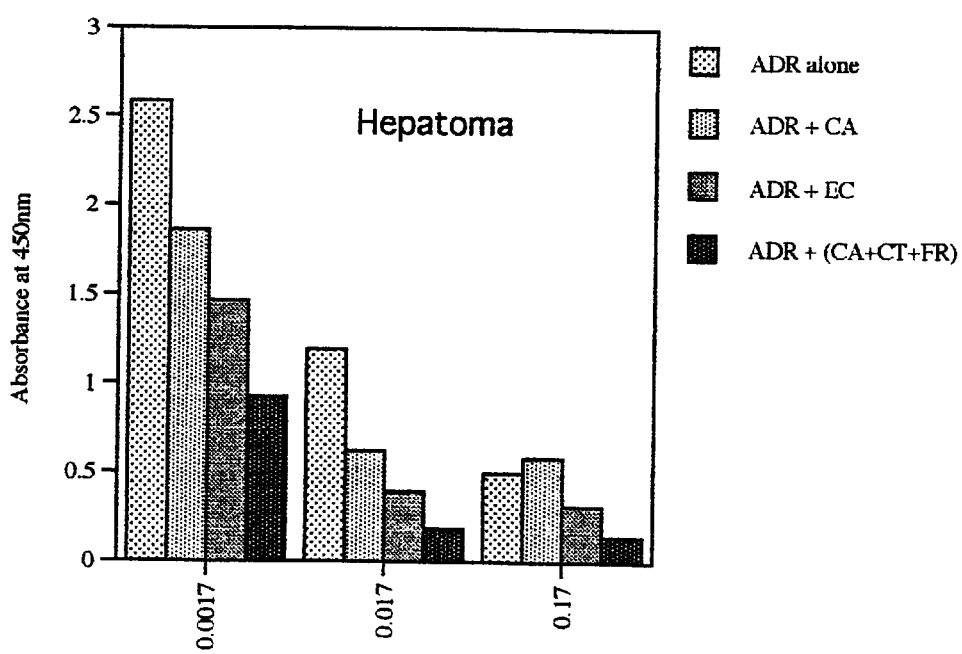
FIG. 4 is a histogram showing the comparative results of combining doxorubicin with either: Calcium ascorbate (CA), Ester C (EC), or with the ascorbate metabolites mixture comprising: Calcium Ascorbate (CA), Calcium Threonate (CT), and 4-Hydroxy-5methyl-3(2H)-furanone (FR) in the following respective ratio, 85:7.5:75.

FIG. 4 shows the relative effects of 0.033% CA, EC and CA+CT+FR on ADR activity in the same experiment. All three ascorbate-containing compositions consistently improve the anti-proliferation activity of low doses of ADR, with EC and the triple ascorbate plus metabolites mix producing greater improvement than CA. Most notably, both EC and CA+CT+FR when used in combination with 0.017 micromolar ADR gives about the same or slightly better anti-neoplastic effect as compared to a 10-fold higher dose (0.17 micromolar) of ADR alone.

Figure 5:
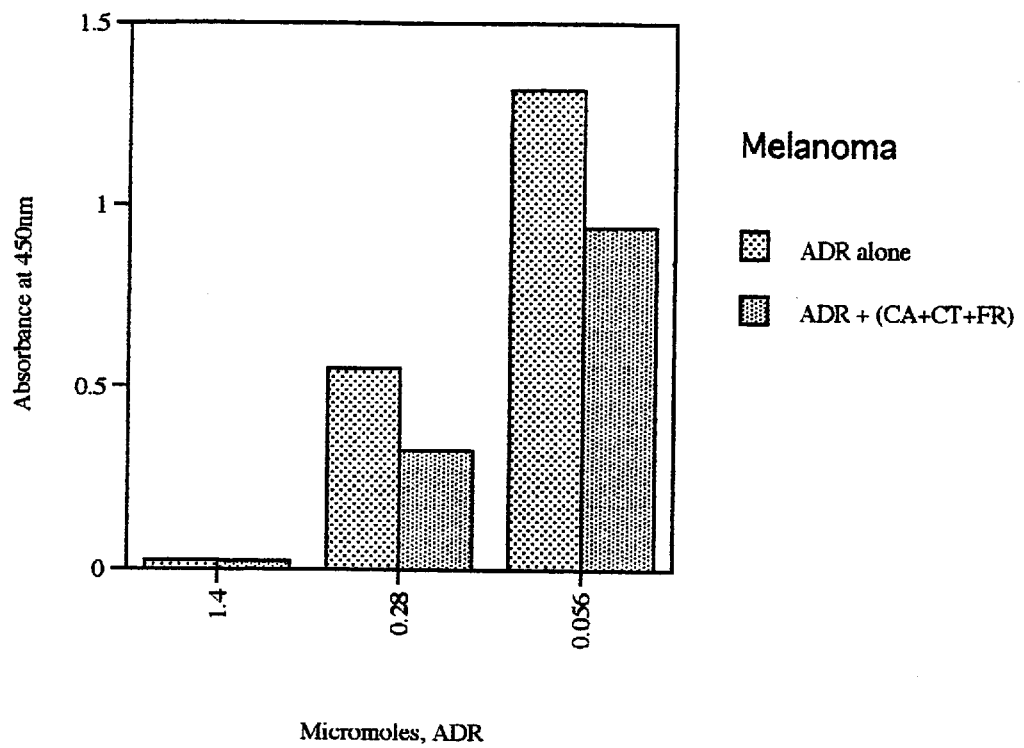
FIG. 5 is a histogram showing a first experiment comparing the results of combining doxorubicin with the ascorbate metabolites mixture (at 33% volume) versus various doses of doxorubicin alone against human melanoma cells.
Figure 6:
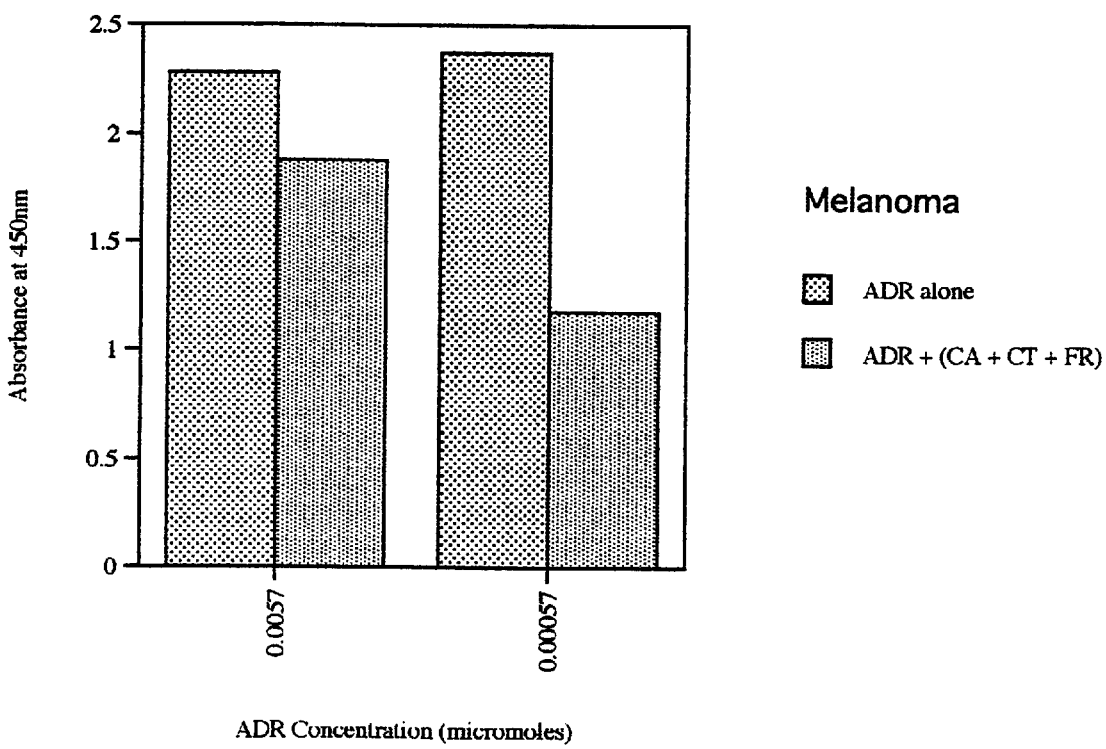
FIG. 6 is a histogram showing a second experiment comparing the results of combining doxorubicin with the ascorbate metabolites mixture (at 33% volume) versus various doses of doxorubicin alone against human melanoma cells.

Effect of Triple Ascorbate plus Metabolites Composition on Anti-Proliferative Activity of Adriamycin in Melanoma Cells FIGS. 5 and 6 show the effects of the triple mix (CA+CT+FR, at 0.033%) plus various doses of ADR against human melanoma cells, from two different tests. In both tests, the triple mix potentiates the anti-neoplastic activity of ADR preferentially at low to moderate doses of the chemotherapeutic drug.

Conclusions

Ascorbate-containing compositions improve the anti-neoplastic activity of cancer chemotherapeutic agents (adriamycin), against both hepatoma and melanoma-derived cell lines as evaluated using a cell-proliferation immunoassay. The enhancing effect is most prominent at low to moderate doses of the chemotherapeutic drug. Compositions containing ascorbate plus metabolites are more effective in enhancing adriamycin activity than ascorbate alone. Triple mixtures containing calcium ascorbate, calcium threonate and furanone (at ratio of 85:7.5:7.5) when combined with low-dose adriamycin suppress tumor cell proliferation at a level similar to or slightly better than a 10-fold higher dose or adriamycin alone. These results indicate the use of ascorbate plus metabolites in combination with low-dose chemotherapy with reduction of drug-associated toxicity.

Having described my invention in such terms as to enable those skilled in the art to understand and practice it and, having identified the presently preferred embodiments there, I claim:

1. A cancer chemotherapeutic composition comprising a cancer chemotherapeutic agent and a potentiating agent selected from the group consisting of Vitamin C metabolites or ascorbic acid-derived furanones, in an amount to potentiate a chemotherapeutic agent.

2. A cancer chemotherapeutic composition comprising a cancer chemotherapeutic agent, a mineral ascorbate, and a potentiating agent selected from the group consisting of Vitamin C metabolites or ascorbic acid-derived furanones, in an amount to potentiate a chemotherapeutic agent.

3. The composition of claim 2, wherein said chemotherapeutic agent is doxorubicin, said metabolite is calcium threonate, said furanone is 4-hydroxy-5-methyl-3(2H)-furanone, and said mineral ascorbate is calcium ascorbate.

4. The method of cancer chemotherapy comprising contacting tumor cells with the composition of claim 1.

5. The method of cancer chemotherapy comprising contacting tumor cells with the composition of claim 2.

6. The method of cancer chemotherapy comprising contacting tumor cells with the composition of claim 3.

* * * * *